United States Patent [19]

Thiele et al.

[11] 4,305,942
[45] Dec. 15, 1981

[54] XANTHINE OXIDASE INHIBITOR AND THERAPEUTIC TREATMENT USING SAME

[75] Inventors: Kurt Thiele; James S. G. Cox, both of Zofingen; Johanna Fischer, Reiden; Ulrich Jahn, Zofingen, all of Switzerland

[73] Assignee: Siegfried Aktiengesellschaft, Switzerland

[21] Appl. No.: 201,500

[22] Filed: Oct. 28, 1980

[30] Foreign Application Priority Data

Nov. 10, 1979 [EP] European Pat. Off. ........ 79104432-4

[51] Int. Cl.$^3$ .............................................. A61K 31/53
[52] U.S. Cl. ..................................... 424/249; 544/183
[58] Field of Search ......................................... 424/249

[56] References Cited

U.S. PATENT DOCUMENTS 3,349,088 10/1967 Molnar et al. ...................... 544/183

FOREIGN PATENT DOCUMENTS 1470296 1/1970 Fed. Rep. of Germany .

OTHER PUBLICATIONS

Merck Index, 9th Ed., (1976) Entry No. 759.

Primary Examiner—Frank Cacciapaglia, Jr.
Attorney, Agent, or Firm—Burns, Doane, Swecker & Mathis

[57] ABSTRACT

Therapeutic xanthine oxidase inhibitor composition containing as an active ingredient 3-dimethylamino-7-methyl-1,2-(n-propylmalonyl)-1,2-dihydro-1,2,4-benzotriazine dihydrate of the formula

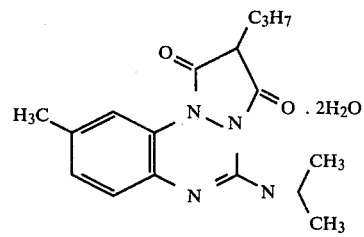

Uratic diathesis in warm-blooded animals is therapeutically treated by administering the aforementioned xanthine oxidase inhibitor to such animals, e.g., human, either orally or by means of an injection, thereby inhibiting their xanthine oxidase activity.

9 Claims, No Drawings

XANTHINE OXIDASE INHIBITOR AND THERAPEUTIC TREATMENT USING SAME

BACKGROUND OF THE INVENTION

The invention concerns a chemotherapeutic agent for inhibiting xanthine oxidase in warm-blooded animals, e.g., humans, and a novel process for therapeutic treatment of uratic diathesis in such animals.

The general term "uratic diathesis" is meant to encompass all different forms of hyperuricaemia, i.e. gout, as caused by disturbances of the purine metabolism.

Irrespective of impressive progress in the field of pharmacotherapy in treating a wide variety of diseases in humans, the chances of treating gout successfully still are extremely low. In spite of a strict diet and a restricted mode of life of the patient in most instances the pathological changes and deformations caused by said disease cannot be stopped. For a pharmacotherapeutic treatment of uratic diathesis a remarkably restricted number of active substances is available. From the chemical point of view the small number of available active substances have no features of their molecular structure in common. For instance, these active substances for treating uratic diathesis include such diverse compounds as benzbromarone (INN), probenecide (INN) and sulfinpyrazone (INN). All of these substances promote the secretion of uric acid by inhibiting the back-resorption of uric acid in the kidney. Thus, these active substances do not and cannot prevent an increased formation of uric acid. Accordingly, the sufficiency of such substances remains restricted. In addition, a long term application of such substances results in a steady overloading of the kidneys with uric acid which in fact is a considerable danger for the kidneys.

Prior Art

The above general situation became somewhat better since the recent introduction of allopurinol (INN) for the therapeutic treatment of uratic diathesis. Since the chemical structure of allopurinol is quite similar to the chemical structure of uric acid, allopurinol is the only known active substance which is really able to lower the uric acid level in the human organism.

Nevertheless, the use of allopurinol has a real disadvantage in that only quite low plasma levels are achievable upon orally administering the standard long term tolerable therapeutical daily dose. This tolerable daily dose for allopurinol is about 300 mg/d. When administering such 300 mg/d dose in one single portion a plasma level of only 2 μg/ml is obtained. This plasma level does not even correspond to three times the in vivo value of the 50% inhibitive concentration (IC 50) for the xanthine oxidase inhibition.

OBJECTS OF THE INVENTION

It is an object of the invention to provide a xanthine oxidase inhibitor drug and a process for therapeutic treatment of uratic diathesis in humans, respectively, allowing for higher relative plasma levels of the active ingredient based on the therapeutically tolerable daily dose as compared to allopurinol.

General Description of the Invention

It has now been discovered that the above object of the invention can be achieved by a xanthine oxidase inhibitor containing as an active ingredient 3-dimethylamino-7-methyl-1,2-(n-propylmalonyl)-1,2-dihydro-1,2,4-benzotriazine dihydrate of the formula

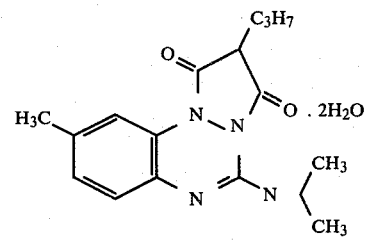

and further containing conventional auxiliary and/or carrier substances and/or conventional supplementary active ingredients.

It has been more particularly discovered that uratic diathesis in humans can be therapeutically treated by inhibiting xanthine oxidase therein by administering to them a composition comprising as a principal active ingredient 3-dimethyl-amino-7-methyl-1,2-(n-propylmalonyl)1,2-dihydro-1,2,4-benzotriazine dihydrate of the formula

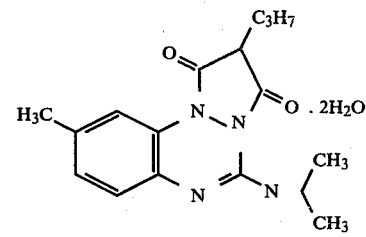

and further containing conventional auxiliary and/or carrier substances and/or conventional supplementary active ingredients.

The above identified active ingredient 3-dimethyl-amino-7-methyl-1,2-(n-propylmalonyl)-1,2-dihydro-1,2,4-benzotriazine dihydrate is known under the WHO recommended International Nonproprietary Name (INN) "azapropazone" (cf. DE 1,470,296 C3 which corresponds to U.S. Pat. No. 3,349,088). Azapropazone is known to have analgetic and antipyretic activities, and it is used as an antiphlogistic drug. For many years azapropazone has been used for the therapeutic treatment of rheumatism in humans. For this purpose, it is usually administered orally in a long term therapeutically tolerable daily dose of 1000 mg/d.

In spite of long years of clinical testing and long years of actual use in medical practice neither the manufacturer of azapropazone nor researchers testing azapropazone nor physicians treating their patients with azapropazone drugs have heretofore become aware of the unexpected and surprising fact that azapropazone has an unprecedentedly high activity as an xanthine oxidase inhibitor. Simultaneously, while azapropazone has been known per se for many years, researchers all over the world have been searching for decades for active substances for fighting gout, and the only active substance they were able to find up to date has been the above-mentioned allopurinol. This, however, allows at maximum tolerable dosages only for relative low levels of the active ingredient in the blood plasma. It thus is a big step forward, and has been totally unexpected for those skilled in the art, that azapropazone can be effectively used as a xanthine oxidase inhibitor in the therapeutic treatment of uratic diathesis in humans. The application of azapropazone as an xanthine oxidase inhibitor drug in the systematic long term therapeutic treatment of uratic diathesis in humans represents a large advantage in the art and a relief for hundreds of thousands of patients suffering from uratic diathesis in its different forms.

Azapropazone is a commercially available product and its preparation is disclosed for instance, in German patent specification DE 1,470,296 C3 which corresponds to U.S. Pat. No. 3,349,088 and, which is expressly incorporated herein by reference. The method of producing azapropazone thus need not be described herein in detail.

In the process for the therapeutic treatment of uratic diathesis the xanthine oxidase inhibitor of the invention is preferably administered orally. However, notwithstanding the fact that the new xanthine oxidase inhibitor is preferably administered orally, it also can be administered in the form of a solution for slow intravenous or intramuscular injection.

For treating an acute attack of uratic diathesis the active xanthine oxidase inhibitor ingredient can be administered to a subject suffering such an attack for the duration of a few days in a daily dosage of up to about 1800 mg/d. For long term treatment of a chronic uratic diathesis the xanthine oxidase inhibitor ingredient of the invention can be administered in a daily dosage of up to about 1000 mg/g. However, in view of the high obtainable plasma levels of the active ingredient such a high long term daily dosage will not ordinarily be necessary. Actually, for the long term treatment of chronic uratic diathesis daily dosages of between about 400 and about 800 mg/d, and preferably a daily dosage in the range of between 500 and 750 mg/d, will be completely successful and satisfactory. Due to the extremely low toxicity of azapropazone no detrimental side effects and no harm resulting from long term treatment are observed especially when the active ingredient is administered in a daily dosage range of between 500 and 750 mg/d.

In contrast, when treating gout by administering allopurinol in long term treatment a far higher risk of harmful side reactions must be run in view of the far higher level of toxicity which must be taken into account due to the very low plasma levels obtainable in such a case. The risk run with the long term administration of allopurinol is that of gastrointestinal disease. This risk is absolutely excluded when administering the xanthine oxidase inhibitor of the invention in a long term dosage range of as low as 400 to 800, especially 500 to 750 mg/d.

In addition to this advantage, while the only beneficial activity of allopurinol is xanthine oxidase inhibition, the active ingredient of the invention shows not only such xanthine oxidase inhibiting activity but also concommitantly a welcome and beneficial analgetic activity when administered for the therapeutic treatment of uratic diathesis.

Representative formulations are described below to exemplify some of the dosage forms in which the xanthine oxidase inhibitor may be employed, but such illustrative examples shall not be considered limiting of the scope of the invention.

EXAMPLE 1

One thousand hard gelatin capsules, each containing 300 mg of azapropazone dihydrate can be prepared from the following types and amounts of ingredients:

| | |
|---|---|
| Azapropazone dihydrate | 300 gm |
| Corn starch | 19 cm |
| Methylcellulose (300 cps) | 3 gm |
| Magnesium stearate | 4 gm |
| Talc | 3 gm |
| Colloidal silicon dioxide | 1 gm |

The azapropazone is mixed with the starch, granulated with a 5% solution of methylcellulose in water, passed through a screen (1 mm mesh-width) and dried carefully. The dried granules are screened, mixed thoroughly with the magnesium stearate, talc and colloidal silicon dioxide and filled into size 1 capsules.

EXAMPLE 2

One thousand film-coated tablets, each containing 600 mg of azapropazone dihydrate can be prepared from the following types and amounts of ingredients:

| | |
|---|---|
| Azapropazone dihydrate | 600 gm |
| Carboxymethyl-starch | 15 gm |
| Colloidal silicon dioxide | 18 gm |
| Microcrystalline cellulose | 30 gm |
| Gelatin | 10 gm |
| Magnesium stearate | 12 gm |
| Talc | 43 gm |
| Hydroxypropylmethylcellulose (low viscosity) | 7.6 gm |
| Titanium dioxide | 2.0 gm |
| Yellow iron oxide pigment | 0.4 gm |
| Polyethyleneglycol 6000 | 2.0 gm |

The azapropazone is mixed thoroughly with the carboxymethylstarch, one third of the colloidal silicon dioxide and the microcrystalline cellulose, then granulated with the gelatin as 4% aqueous solution.

The moist mass is passed through a screen (1 mm mesh-width) and dried carefully. The dried granules are screened, mixed thoroughly with the magnesium stearate, the remainder of the colloidal silicon dioxide and the talc then pressed into 740 mg tablets. The tablets are coated by spraying on a suspension of the titanium dioxide and iron oxide pigment in an aqueous solution of hydroxypropylmethylcellulose and polyethylene glycol. Coating may be carried out in a conventional coating pan or in suitable equipment for coating in a fluid bed.

EXAMPLE 3

One thousand vials each containing the equivalent of 660 mg azapropazone dihydrate (freeze dried for reconstitution with 5 ml water for injection to give a solution containing the equivalent of 120 mg azapropazone dihydrate per ml of injection solution) can be prepared as follows:

| | | |
|---|---|---|
| Azapropazone dihydrate | | 660.0 gm |
| Mannitol | | 33.0 gm |
| Sodium hydroxide | approx. | 59.2 gm |
| Water for injection q.s. | to | 3.000 ml |

Dissolve the mannitol in about 900 ml of water with slight heating, add the azapropazone dihydrate and mix to disperse. Dissolve the sodium hydroxide in about 900 ml of water and add the warm solution carefully to the azapropazone dispersion and stir until dissolved. Add water to about 2900 ml and mix, determine pH and adjust if necessary with sodium hydroxide solution to pH 9.7. Make up to volume with water. Filter the solution through a sterile membrane filter and fill 3.0 ml of solution into sterile vials under aseptic conditions. Freeze dry under aseptic conditions under reduced pressure and stopper the vials in the drying chamber after raising the pressure to 0.67 mbar by admission of sterile, dry nitrogen.

The solution prepared by dissolution of the contents of one vial in 5.0 ml of water for injection is suitable for slow intravenous injection. For intramuscular injection 3.0 ml of solvent is preferred and the sterile solvent may contain benzyl alcohol, cinchocaine hydrochloride or other suitable local anesthetic in appropriate concentration.

Tests

The xanthine oxidase inhibiting activities of azapropazone as the novel active ingredient and of allopurinol as the sole known or most favored active ingredient according to the prior art are tested in vitro for comparison.

In the human in vivo metabolism the xanthine oxidase decomposes xanthine and hypoxanthine, respectively, to yield uric acid. This decomposition reaction can be perfectly simulated in vitro. For this purpose buffered solutions of (a) hypoxanthine, (b) xanthine oxidase and (c) the test substance are prepared. Solution (a) and (c) are mixed and filled into the cuvette of a UV-spectrophotometer. Solution (b) is then added into the cuvette. The UV-spectrophotometer is adjusted to 290 nm, i.e. to one of the main absorption lines of uric acid. Registration of the intensity of the 290 nm line is commenced immediately upon adding solution (b), i.e., upon adding the xanthine oxidase solution. The measurement is continued for exactly 6 minutes. For each test substance a certain number of measurements is carried out at varying concentrations of the test substance. The registered intensity values obtained after a certain time, here after 6 minutes, are compared to a standard registration containing as a solution (c) a blank buffer solution.

For the present measurements the UV-spectrophotometer used is a ZEISS PM Q II.

Solution (a) is 1 ml hypoxanthine puriss (FLUKA No. 56700) dissolved in a concentration of $1.5 \times 10^{-4}$ moles/liter in a 0.067 molar phosphate buffer solution having a pH of 7.4.

Solution (b) is 1 ml xanthine oxidase (CALBIOCHEM No. 682151) having a specific activity of 2.65 I.U./ml at 30° C., and is diluted in a ratio of 1:200 in the same phosphate buffer as used in solution (a).

Solution (c) is 1 ml of blank phosphate buffer for controls (standards) and a solution of the test substance dissolved in said phosphate buffer in varying concentrations, respectively.

The spectrophotometric measurements are carried out at ambient temperature.

Using test substance concentrations in the range of about $10^{-4}$ to $10^{-6}$ moles/liter based on the concentration in the cuvette after mixing solutions (a), (b) and (c), the gradient of the optical density with time is in the order of 0.08 to 0.1 $\min^{-1}$.

With reference to the standard the following values of xanthine oxidase inhibition are measured for azapropazone:

| Concentration of azapropazone (moles/liter) | Inhibition (%) |
|---|---|
| standard | 0 |
| $1.25 \times 10^{-5}$ | 20 |
| $2.50 \times 10^{-5}$ | 35 |
| $5.00 \times 10^{-5}$ | 55 |

From such values a 50% inhibitive concentration of $IC50 = 4.0 \times 10^{-5}$ moles/liter is interpolated.

In a completely analogous manner a value of $IC50 = 5.0 \times 10^{-6}$ moles/liter is obtained for allopurinol.

In other words, the 50% inhibition concentration for azapropazone is 13.5 μg/ml and is only 0.7 μg/ml for allopurinol, respectively.

From Arzneim.-Forsch. (Drug Res.) 23 (1973), pages 920–921, it is known that a plasma level of 80.8 μg/ml is obtained when administering in one single portion the long term therapeutically tolerable daily dosage of 1000 mg/d azapropazone orally. From Handbook of Experimental Pharmacology 51 (1978), pages 485–514, it is known that a plasma level of 2.0 μg/ml is obtained when administering orally in one single portion the long term therapeutically tolerable daily dosage of 300 mg/d allopurinol.

Comparing the plasma levels obtainable with the tolerable daily dosage to the 50% inhibitive concentration one finds that the azapropazone level is six times higher than the IC50, while the allopurinol level is only 2.9 times higher than the 50% inhibitive concentration.

In other words, for obtaining equal plasma levels, i.e. for obtaining comparable activities as to the xanthine oxidase inhibition, only half the maximum therapeutically tolerable daily dosage is required for azapropazone whereas a dosage corresponding to exactly the maximum therapeutically tolerable daily dosage is required where allopurinol is administered.

What is claimed is:

1. A process for the therapeutic treatment of a warm blooded animal suffering from uratic diathesis which process comprises administering to said animal, in an amount effective to inhibit xanthine oxidase therein, a composition comprising as a principal active ingredient a compound of the formula

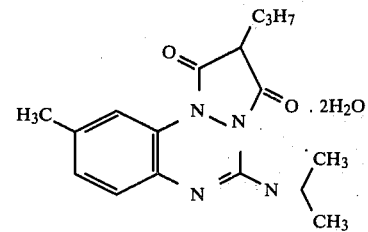

2. The process of claim 1 wherein said composition further comprises a member selected from the group consisting of carboxymethyl-starch, corn starch, colloidal silicon dioxide, microcrystalline cellulose, methylcellulose, hydroxypropylmethylcellulose, gelatin, magnesium stearate, talc, polyethyleneglycol, titanium dioxide, yellow iron oxide pigment, and mixtures thereof.

3. The process of claim 1 wherein said composition is administered orally.

4. The process of claim 1 wherein said composition comprises a mixture containing starch, cellulose, magnesium stearate, colloidal silicon dioxide and talc as a carrier.

5. The process of claim 1 wherein said principal active ingredient is administered in a daily dosage range of between 400 and 800 mg/d to a human suffering chronic uratic diathesis.

6. The process of claim 5 wherein said principal active ingredient is administered in a daily dosage range of between 500 and 750 mg/d.

7. The process of claim 1 wherein said composition comprises a mixture of mannitol, sodium hydroxide and water having a pH of greater than 7 and less than 10 as a solvent wherein said principal active ingredient is dissolved, and wherein said composition is administered by injection.

8. The process of claim 7 wherein said composition is administered by intravenous injection.

9. The process of claim 7 wherein said composition is administered by intramuscular injection.

* * * * *